United States Patent [19]

Herrling

[11] 4,237,136

[45] Dec. 2, 1980

[54] PHARMACEUTICAL COMPOSITIONS AND METHODS OF USING THIADIAZOLO PYRIMIDINONE COMPOUNDS

[76] Inventor: Siegfried Herrling, Dohlenweg 33, Stolberg, Fed. Rep. of Germany, 5190

[21] Appl. No.: 803,296

[22] Filed: Jun. 3, 1977

[30] Foreign Application Priority Data

Jun. 4, 1976 [DE] Fed. Rep. of Germany ....... 2625117
Jun. 4, 1976 [DE] Fed. Rep. of Germany ....... 2625118

[51] Int. Cl.³ .................... A61K 31/505; C07D 513/04
[52] U.S. Cl. .................................... 424/251; 544/278; 546/271

[58] Field of Search .................... 260/256.5 R, 251 A; 424/251

[56] References Cited

U.S. PATENT DOCUMENTS 3,813,360  5/1974  Evans ................................ 260/25 A Primary Examiner—Donald G. Daus
Assistant Examiner—Lisa Jones
Attorney, Agent, or Firm—Weiser, Stapler & Spivak

[57] ABSTRACT

Substituted 7H-thiazolo- and 7H-thiadiazolo-pyrimidine-7-ones compounds and the drug composition containing same. The compounds are immunostimulants for mammals. A process of making these compounds and of using the drug composition.

34 Claims, No Drawings

PHARMACEUTICAL COMPOSITIONS AND METHODS OF USING THIADIAZOLO PYRIMIDINONE COMPOUNDS

This invention relates to certain compounds, which are substituted 7H-thiazolo and 7H-thiadiazolo-pyrimidine-7-ones, and to medicaments which contain one or more compounds as active principles. The compounds correspond to the formula

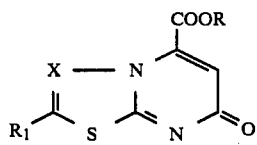

in which
X represents nitrogen atom or the group

R represents hydrogen, a pharmaceutically acceptable cation or an alkyl radical of 1 to 5 carbon atoms, $R_1$ and $R_2$ are the same or different and represent hydrogen, an alkyl radical of 1 to 5 carbon atoms or aralkyl, phenyl, thienyl or pyridyl radicals, optionally substituted by halogen atoms, alkyl or alkoxy radicals with up to 4 carbon atoms in the alkyl radical, or cycloalkyl radicals containing 5 to 7 carbon atoms and/or pharmaceutically useable salts of these compounds.

It has surprisingly been found that the compounds of formula I show pronounced activity in stimulating the immune system and, by virtue of this property, are valuable therapeutic agents for diseases where an increase in the body's defenses is required, especially when the immunity of the diseased organism is disturbed or inadequately developed. Examples of diseases such as these which can be treated with the medicaments according to the invention are virus infections, bacterial infections, systemic lupus erythematosis, and tumors. They can be used also for preventing metastasis, etc.

The immunity-stimulating effect was experimentally determined as follows:

(a) Study of phagocytosis performances in vitro:

Doses of 1, 5, 10 and 15 mg of 7H-thiazolo-[3,2-a]-pyrimidin-7-one-5-carboxylic acid, (hereinafter referred to as "substance A") or, for example, 3-phenyl-5-carbethoxy-7H-thiazolo-[3,2-a]-pyrimidin-7-one, (hereinafter referred to as "substance B") per kg of body weight were orally administered to groups of 20 mice. The mice thus treated together with 20 untreated control animals were then sacrificed and the peritoneal macrophages and polymorphonuclear leucocytes flushed out from the abdominal cavity with tissue culture media. The cells were washed, adjusted to the same number per volume in the individual samples and incubated for 1, 2 and 3 hours either with latex particles or with pathogenic staphylococci. The cells are then washed again, applied to specimen holders and colored. The phagocytosis index is determined by counting out the cells laden with latex particles or with staphylococci in relation to the free cells.

It is also possible to inject the test animals intraperitoneally with the test substances in the various doses 1 hour before the beginning of the test and then to proceed in the manner described above.

In either way, an impressive increase in phagocytosis is obtained by administering the above-mentioned substances, values of up to about 150% of the phagocytosis indexes determined on cells of untreated control animals being observed.

(b) Study of the phagocytosis performances in vivo:

Groups of 20 mice are pretreated with substance A or substance B in the same way as described in (a). Three days after the substance has been administered, the test animals are injected intraperitoneally with latex particles or staphylococci. The animals are then killed in corresponding sub-groups 1, 2 and 3 hours after the injection of the particles to be phagocytosed. The peritoneal cells are removed, washed, applied to specimen holders by means of a cytocentrifuge and subsequently colored. By determining the phagocytosis indexes, the phagocytosis-stimulating influence of substances A and B was confirmed by this method, too.

Corresponding results were also obtained when the substances mentioned above were replaced by other compounds corresponding to formula I such as, for example, 2-methyl-3-phenyl-7H-thiazolo-[3,2-a]-pyrimidin-7-one-5-carboxylic acid ethyl ester, 3-(p-tolyl)-7H-thiazolo-[3,2-a]-pyrimidin-7-one-5-carboxylic acid ethyl ester, 2-methyl-3-(p-bromophenyl)-7H-thiazolo-[3,2-a]-pyrimidin-7-one-5-carboxylic acid ethyl ester, etc.

(c) Stimulation of immunoglobulin-G-receptor activity on the macrophage surface:

Single doses of 0.1, 1 or 10 mg of the substance to be tested per kg of body weight are administered subcutaneously to groups of female mice weighing between 18 and 20 g. After 24 hours, the animals are killed and the peritoneal macrophages are flushed out from the abdominal cavity with a cell culture medium containing 10% of calf's serum, adjusted to a density of $10^6$ cells/ml, placed in Petri dishes (5 cm in diameter) in volumes of 3 ml and incubated in an incubation cabinet for 4 hours at 37° C. The cells which do not adhere to the glass are carefully washed off with cell culture medium. Thereafter, 3 ml of a 0.1% suspension of human erythrocytes of blood group $A_1$ are introduced into each Petri dish. These erythrocytes had been previously incubated for 30 minutes at room temperature with the serum (diluted with cell culture medium in a ratio of 1:50) of 80-day-old female C 57 BL/10-mice, whereby they were charged with the specific "natural" antibody formed by the female C 57 BL/10-mouse. The macrophages adhering to the Petri dish bind the human erythrocytes thus pretreated to different extents, depending upon the immunoglobulin-G-receptor activity at their surface.

It was found that the macrophages of animals pretreated with the substances of formula I bind significantly more (antibody-laden) erythrocytes than the macrophages of untreated animals, the differences often amounting to several hundred percent.

In order to demonstrate the effects against virus infections, mice were infected with herpes viruses and with hepatitis viruses (murine). They were then given oral doses of substance A for 1 or more days with the following results (the figures quoted in the Table indicate the percentages of surviving animals; of untreated, infected control animals, only 10 to 20% survived the infection):
Infection with herpes viruses:
(Treatment begins at the same time as infection)

| Treatment time | Dose (mg of active principle/kg of body weight) | |
| --- | --- | --- |
|  | 1 | 10 |
| 1 day | 50 | 60 |
| 5 days | 60 | 70 |

Infection with hepatitis viruses (murine)
(Therapy begins 24 hours after infection)

| Treatment time | Dose (mg of active principle/kg of body weight) | | |
| --- | --- | --- | --- |
|  | 0.5 | 1.0 | 5.0 |
| 1 day | a | 30 | 40 |
| 5 days | 40 | 50 | 50 |
| 10 days | 60 | 60 | a | a not tested

In further tests, mice were infected with hepatitis viruses (murine) and, 24 hours later, were treated with test substances in the single (oral) doses shown in the following Table. The survival rates quoted in the Table were obtained for the treated animals, whilst from 80 to 100% of untreated, infected control animals died:

| R | $R_1$ | X | $R_2$ | Dose (mg/kg) | % surviving animals |
| --- | --- | --- | --- | --- | --- |
| $C_2H_5$ | H | $R_2-\underset{\parallel}{C}-$ | phenyl | 0.5 | 60–70 |
| $C_2H_5$ | $CH_3$ | $R_2-\underset{\parallel}{C}-$ | phenyl | 0.5 | 60 |
| $C_2H_5$ | H | $R_2-\underset{\parallel}{C}-$ | $CH_3$–phenyl | 1.0 | 50 |
| $C_2H_5$ | H | $R_2-\underset{\parallel}{C}-$ | $C_2H_5$–phenyl | 1.0 | 60 |
| $C_2H_5$ | $CH_3$ | $R_2-\underset{\parallel}{C}-$ | Br–phenyl | 0.1 | 50 |
| $CH_3$ | H | N | — | 0.1 | 60 |
| $C_2H_5$ | phenyl | N | — | 0.5 | 50–60 |

These test results demonstrate the surprising therapeutic value of the compounds corresponding to formula I, especially for the treatment of virus infections as well.

British Pat. No. 1,345,148 published Jan. 30, 1974, discloses certain pyrimidinobenzothiazolones, substituted-imino-$\Delta^4$-thiazolines and substituted iminobenzothiazolines and thiazolopyrimidinones, in particular in Example 5, the 3-methyl-5-carbomethoxy-7H-thiazolo-[3,2-a]-pyrimidin-7-one. It is disclosed that the compounds are antifungal, antimycotic, amoebicidal and antiinflammatories.

In contrast, compound A of this invention was ineffective on *Aspergillus parasiticus*, *Candida albicans*, *Sporotrichon Beurmannii* and *Trichophyton gypseum*, even in the high concentration of 100 mcg/ml.

The compounds of the invention are useful in the smallest amount which is effective to stimulate an immunological effect. Though, if desirable, lower dosage can be used, a dosage in the range of about 0.1 mg/kg to about 15 mg/kg has been found suitable.

The drugs according to the invention contain one or more of the active compositions disclosed in such a quantity that the daily dose amounts up to from 5 to about 1500 mg and preferably between about 25 and about 500 mg. Individual preferred dosage is from about 10 to about 250 mg. The treatment is best carried out with 2 to 3 single doses per day. Suitable formulations for oral administration are standard tablets, dragrees, syrups, drops and other pharmaceutical formulations commonly used for oral therapy, including for example those from which the active principles are released with delay.

However, the medicaments according to the invention may also be applied in the form of suppositories produced in the usual way.

Since the active principles of formula I, particularly when R represents a pharmaceutically acceptable cation, are readily soluble in water and represent adequately stable substances, the medicaments according to the invention also include sterile, injectable solutions of these active principles.

Other formulations according to the invention include sprays, especially for intranasal application.

The present invention also relates to the new heterocyclic compounds corresponding to the formula

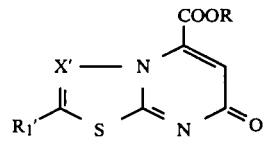

Ia in which
R has the same meaning as in formula I,
X' represents a nitrogen atom or the group

$R'_1$ and $R'_2$ are the same or different and, with the proviso that $R'_1$ cannot represent hydrogen when $R'_2$ is hydrogen or methyl and that X' cannot represent a nitrogen atom when $R'_1$ is a methyl group, represent hydrogen, alkyl radicals with 1 to 5 carbon atoms or aralkyl, phenyl, thienyl or pyridyl radicals optionally substituted by halogen atoms, alkyl or alkoxy radicals with up to 4 carbon atoms in the alkyl radical, or cycloalkyl radicals containing 5 to 7 carbon atoms,
and to pharmaceutically useable salts of these compounds which represent a preferred group of the compounds of formula I.

When it represents an alkyl radical, R preferably contains 1 or 2 carbon atoms.

The aralkyl radicals in question are, in particular, the benzyl and phenyl ethyl radicals.

In cases where at least one of the substituents $R_1$, $R_2$ or $R'_1$, $R'_2$ contain halogen atoms, the halogen atoms in question are preferably fluorine, chlorine or bromine atoms.

The compounds corresponding to formula Ia are obtained by reacting a 2-aminothiazole or 2-amino-1,3,4-thiadiazole corresponding to the formula

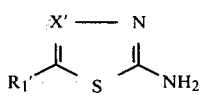

in which R'₁ and X' have the same meaning as above, with an acetylene dicarboxylic acid dialkyl ester derived from an alkanol containing from 1 to 5 carbon atoms.

In cases where the group —COOR in a compound of formula I is intended to represent a carboxyl group or a salt derived therefrom, whilst R represents an alkyl radical containing from 1 to 5 carbon atoms, it is readily possible to saponify the ester group then present and optionally to convert the resulting compound of formula I containing a free carboxyl group into pharmaceutically useable salts by reaction with suitable bases. Salts such as these are, in particular, alkali, alkaline earth and ammonium salts of the compounds of formula I.

The compounds of formula I are capable of forming salts with acids, particularly when R represents an alkyl radical containing from 1 to 5 carbon atoms. Pharmaceutically useable salts such as these are, for example, the formates, acetates, propionates, hydrochlorides, hydrobromides, sulfates, phosphates, etc. There can be used any acids which form pharmaceutically acceptable salts, like strong organic and strong inorganic acids, (mono and dibasic acids) like formic, acetic, propionic, phosphoric, nitric, hydrochloric, hydrobromic, malonic, glycolic acid, salicylic and, benzene- or toluenesulfuric acid, bromo- or chloro-benzoic and, maleic or fumaric acid, citric and other equivalent acids.

The reaction of the compound of formula II with the acetylene dicarboxylic acid dialkyl ester is carried out in the presence of a solvent or suspending agent, optionally at elevated temperature. Suitable solvents or suspending agents are, for example, lower aliphatic alcohols, especially methanol, ethanol and propanols, acetic acid ethyl or propyl ester, acetonitrile, tetrahydrofuran, dioxane, chlorobenzene, dimethyl formamide, etc. It is also possible with advantage initially to react the reactants in ethanol for example and then to complete the ring-closing reaction by heating in a solvent of higher boiling point, for example chlorobenzene. If at least one of the radicals R₁ and R₂ represents a pyridyl radical, the condensation reaction is best carried out in the presence of at least one mole of an acid, preferably acetic acid.

The formation of resin-like, dark coloured by-products can be largely avoided by working in the absence of light and air.

The production of the compounds is illustrated by the following examples. All the temperatures quoted are uncorrected.

The examples are not to be construed as a limitation of the invention.

EXAMPLE 1

17.6 g of 2-amino-4-phenylthiazole are dissolved in 100 ml of tetrahydrofuran, the resulting solution is cooled to approximately 15° C. and 17.5 g of acetylene dicarboxylic acid diethyl ester are slowly added to it with stirring at that temperature. The mixture is left standing for 3 days, after which the crystals formed are filtered off the quantity of which was increased by concentrating the mother liquor to approximately half its original volume and recrystallized from ethanol. 3-Phenyl-7H-thiazolo-[3,2-a]-pyrimidin-7-one-5-carboxylic acid ethyl ester is thus obtained in a yield of 16.9 g, corresponding to 56.3% of the theoretical.

Melting point: 173°–175° C.

| | $C_{15}H_{12}N_2O_2S$ (300.34) | | | |
|---|---|---|---|---|
| | C | H | N | S |
| calculated: | 60.0% | 4.03% | 9.34% | 10.6% |
| observed: | 59.7% | 4.30% | 9.60% | 10.5% |

3-Phenyl-7H-thiazolo-[3,2-a]-pyrimidin-7-one-5-carboxylic acid methyl ester, which melts at 195°–199° C. with decomposition, is similarly obtained from acetylene dicarboxylic acid dimethyl ester.

EXAMPLE 2

The procedure is as in Example 1, except that 19 g of 2-amino-4-phenyl-5-methylthiazole are used. 2-Methyl-3-phenyl-7H-thiazolo-[3,2-a]-pyrimidin-7-one-5-carboxylic acid ethyl ester melting at 161° to 163° C. after recrystallization from ethyl acetate is obtained in this way.

| | $C_{16}H_{14}N_2O_3S$ (314.37) | | |
|---|---|---|---|
| | C | H | N |
| calculated: | 61.1% | 4.49% | 8.92% |
| observed: | 60.7% | 4.46% | 8.61% |

EXAMPLE 3

The procedure is as in Example 1, except that ethanol is used as solvent in place of tetrahydrofuran, the air is displaced from the reaction vessel by nitrogen and the reaction mixture is stored in darkness. In this way, the product is obtained in substantially pure form in a yield of 86.4% of the theoretical.

EXAMPLE 4

9.5 g of 2-amino-4-(p-tolyl)-thiazole are reacted with 8.7 g of acetylene dicarboxylic acid diethyl ester in 100 ml of tetrahydrofuran in the same way as described in Example 1.

The reaction mixture is concentrated, the residue is dissolved in ethyl acetate and ligroin is added to the resulting solution. 3-(p-Tolyl)-7H-thiazolo-[3,2-a]-pyrimidin-7-one-5-carboxylic acid ethyl ester melting at 122°–125° C. (decomposition) is obtained.

| | $C_{16}H_{14}N_2O_3S$ (314.37) | | | |
|---|---|---|---|---|
| | C | H | N | S |
| calculated: | 61.1% | 4.49% | 8.92% | 10.18% |
| observed: | 60.7% | 4.60% | 8.67% | 9.87% |

EXAMPLE 5

The procedure is as in Example 1, except that 9.4 g of 2-amino-4-(p-bromophenyl)-5-methyl thiazole and 5.95 g of acetylene dicarboxylic acid diethyl ester are used. 2-methyl-3-(p-Bromophenyl)-7H-thiazolo-[3,2-a]-pyrimidin-7-one-5-carboxylic acid ethyl ester melting at 217° to 220° C. (decomposition) is obtained.

|  | $C_{16}H_{13}BrN_2O_3S$ (393.27) | | | |
| --- | --- | --- | --- | --- |
|  | C | H | N | S |
| calculated: | 48.75% | 3.33% | 7.12% | 8.13% |
| observed: | 48.75% | 3.30% | 6.85% | 8.02% |

EXAMPLE 6

The reaction of 12.2 g of 2-amino-4-(2',4'-dichlorophenyl)-thiazole with 8.5 g of acetylene dicarboxylic acid diethyl ester in the presence of 150 ml of ethanol in accordance with Example 3 gives 3-(2',4'-dichlorophenyl)-7H-thiazolo-[3,2-α]-pyrimidin-7-one-5-carboxylic acid ethyl ester which melts at 180°–192° C. with decomposition.

|  | C | H | N | S |
| --- | --- | --- | --- | --- |
| calculated: | 48.78% | 2.72% | 7.57% | 8.67% |
| observed: | 48.82% | 2.75% | 7.56% | 8.53% |

EXAMPLE 7

10 g of 2-amino-4-(4'-ethylphenyl)-thiazole are dissolved in 50 ml of ethanol and 8.4 g of acetylene dicarboxylic acid diethyl ester are added to the resulting solution. After standing overnight, the mixture is concentrated by evaporation in vacuo to dryness at a bath temperature of 40° to 50° C. 50 ml of chlorobenzene are added to the residue, followed by heating unter reflux for 1 hour. After concentration by evaporation in vacuo, the residue is dissolved in ether, treated with carbon, filtered and petroleum ether subsequently added. The product precipitating is washed with a little ether and dried. 3-(4'-ethylphenyl)-7H-thiazolo-[3,2-a]-pyrimidin-7-one-5-carboxylic acid ethyl ester melting at 142°–144° C. is thus obtained.

|  | C | H | N | S |
| --- | --- | --- | --- | --- |
| calculated: | 62.17% | 4.91% | 8.53% | 9.75% |
| observed: | 62.04% | 4.83% | 8.26% | 9.46% |

EXAMPLE 8

8.5 g of 2-amino-4-(3',4'-dimethoxyphenyl)-thiazole and 6.1 g of acetylene dicarboxylic acid diethyl ester are introduced into 100 ml of ethanol. After the air in the reaction vessel has been displaced by nitrogen, the mixture is heated to approximately 50° C. until a clear solution is obtained. After standing for 2 days at room temperature, the solution thus obtained is concentrated in vacuo to dryness. The residue is washed with ethylacetate and then with ether and subsequently dried. The 3-(3',4'-dimethoxyphenyl)-7H-thiazolo-[3,2-a]-pyrimidin-7-one-5-carboxylic acid methyl ester thus obtained melts at 172° to 174° C. with decomposition.

|  | $C_{12}H_{16}N_2O_5S$ (360.4) | | | |
| --- | --- | --- | --- | --- |
|  | C | H | N | S |
| calculated: | 56.65% | 4.47% | 7.78% | 8.88% |
| observed: | 55.93% | 4.84% | 7.51% | 8.80% |

EXAMPLE 9

A mixture of 12.8 g of 2-amino-4,5-dimethylthiazole, 150 ml of ethanol and 17 g of acetylene dicarboxylic acid diethyl ester is heated to approximately 30° C., producing a weakly exothermic reaction. The mixture is left standing overnight, subsequently concentrated in vacuo to dryness and the residue is boiled for 1 hour with 100 ml of chlorobenzene. After concentration by evaporation in vacuo, the residue is treated with ethyl acetate, crystallization occurring. The product is filtered off under suction, washed with ether and dried. The 2,3-dimethyl-7H-thiazolo-[3,2-a]-pyrimidin-7-one-5-carboxylic acid ethyl ester thus obtained melts at 140° to 142° C.

|  | $C_{11}H_{12}N_2O_3S$ (252.3) | | | |
| --- | --- | --- | --- | --- |
|  | C | H | N | S |
| calculated: | 52.35% | 4.79% | 11.09% | 12.69% |
| observed: | 52.43% | 4.72% | 10.97% | 12.93% |

EXAMPLE 10

100 ml of tetrahydrofuran are added to 10.1 g of 2-amino-1,3,4-thiadiazole, followed by the gradual introduction of 14.2 g of acetylene dicarboxylic acid dimethyl ester. The reaction mixture is left standing for 3 days, resulting in the formation of a clear, yellow colored solution. The solution thus formed is concentrated by evaporation in vacuo to dryness. Recrystallization of the residue from ethyl acetate gives 7H-1,3,4-thiadiazolo-[3,2-a]-pyrimidin-7-one-5-carboxylic acid methyl ester melting at 134° C. with decomposition.

|  | C | H | N | S |
| --- | --- | --- | --- | --- |
| calculated: | 39.80% | 2.39% | 19.90% | 15.18% |
| observed: | 39.70% | 2.44% | 19.66% | 15.11% |

EXAMPLE 11

A mixture of 10 g of 2-amino-5-phenyl-1,3,4-thiadiazole, 100 ml of ethanol and 9.6 g of acetylene dicarboxylic acid diethyl ester is heated in a water bath until a clear solution has formed. 2-Phenyl-7H-1,3,4-thiadiazolo-[3,2-a]-pyrimidin-7-one-5-carboxylic acid ethyl ester crystallizes out on standing overnight, being filtered off under suction and washed with a little ethanol. Melting point: 169°–172° C.

|  | C | H | N | S |
| --- | --- | --- | --- | --- |
| calculated: | 55.80% | 3.68% | 13.95% | 10.64% |
| observed: | 55.65% | 3.80% | 14.00% | 10.87% |

EXAMPLE 12

11.5 g of 2-amino-5-(p-methoxyphenyl)-1,3,4-thiadiazole are reacted with 9.5 g of acetylene dicarboxylic acid diethyl ester in 100 ml of ethanol in the same way as described in Example 11. 7 g of the crude 2-(p-methoxphenyl)-7H-1,3,4-thiadiazolo-[3,2-a]-pyrimidin-7-one-5-carboxylic acid ethyl ester thus obtained, melting at 216°–218° C., are introduced into a solution of 1.3 g of potassium hydroxide in 200 ml of ethanol. The reaction mixture is briefly boiled and then left standing overnight. The crystals precipitated are dissolved by the addition of water. After acidification with hydrochloric acid to approximately pH 2, the crystals are filtered off under suction, washed with water and dried. 2-(p-Methoxyphenyl)-7H-1,3,4-thiadiazolo-[3,2-a]-pyrimidin-7-one-5-carboxylic acid melting with decomposition at 227°–230° C. is thus obtained.

|  | C | H | N | S |
|---|---|---|---|---|
| calculated: | 51.53% | 2.99% | 13.87% | 10.58% |
| observed: | 51.16% | 3.04% | 13.61% | 10.57% |

EXAMPLE 13

The procedure is as in Example 12, except that 13.2 g of 2-amino-5-(3',4'-dimethoxyphenyl)-1,3,4-thiadiazole are used instead of 2-amino-5-(p-methoxyphenyl)-1,3,4-thiadiazole, 2-(3',4'-dimethoxyphenyl)-7H-1,3,4-thiadiazolo-[3,2-a]-pyrimidin-7-one-5-carboxylic acid ultimately being obtained. Melting point: 150° C. with decomposition.

|  | C | H | N | S |
|---|---|---|---|---|
| calculated: | 50.40% | 3.33% | 12.62% | 9.62% |
| observed: | 49.95% | 3.40% | 12.74% | 9.45% |

EXAMPLE 14

The reaction of 9.7 g of 2-amino-5-(3', 4', 5'-trimethoxyphenyl)-1,3,4-thiadiazole with 6.2 g of acetylene dicarboxylic acid dimethyl ester in 200 ml of ethanol in accordance with Example 12 gives 2-(3',4',5'-trimethoxyphenyl)-7H-1,3,4-thiadiazolo-[3,2-a]-pyrimidin-7-one-5-carboxylic acid ethyl ester which, as a crude product, melts at 205°–207° C. with decomposition and which is converted as described in Example 12 into the corresponding free acid melting at 220°–223° C. with decomposition.

|  | C | H | N | S |
|---|---|---|---|---|
| calculated: | 49.57% | 3.61% | 11.57% | 8.83% |
| observed: | 49.36% | 4.00% | 11.21% | 9.09% |

EXAMPLE 15

A mixture of 4.5 g of 2-amino-5-(thienyl-2')-1,3,4-thiadiazole, 100 ml of 95% ethanol and 4.2 g of acetylene dicarboxylic acid diethyl ester is left standing overnight, subsequently boiled for 30 minutes and then left to cool. The product is filtered off under suction, recrystallised from ethanol and finally washed with ether and dried. 2-(Thienyl-2')-7H-1,3,4-thiadiazolo-[3,2-a]-pyrimidin-7-one-5-carboxylic acid ethyl ester is obtained in the form of its monohydrate. Melting point: 184°–186° C. with decomposition.

|  | C | H | N | S |
|---|---|---|---|---|
| calculated: | 44.30% | 3.39% | 12.92% | 19.72% |
| observed: | 43.87% | 3.71% | 12.87% | 19.13% |

EXAMPLE 16

A mixture of 6.5 g of 2-amino-5-(pyridyl-4')-1,3,4-thiadiazole, 100 ml of glacial acetic acid and 6.3 g of acetylene dicarboxylic acid diethyl ester is briefly heated to 60° C. and then left standing for 1 day. After concentration by evaporation to dryness, the residue is treated with a little ethyl acetate, filtered under suction and recrystallized from a little ethanol. 2-(pyridyl-4')-7H-1,3,4-thiadiazolo-[3,2-a]-pyrimidin-7-one-5-carboxylic acid ethyl ester melting at 185°–187° C. with decomposition is thus obtained.

|  | C | H | N | S |
|---|---|---|---|---|
| calculcated | 51.65% | 3.31% | 18.53% | 10.60% |
| observed: | 51.74% | 3.27% | 18.20% | 10.64% |

EXAMPLE 17

8.9 g of 2-amino-5-(pyridyl-3')-1,3,4-thiadiazole, 50 ml of glacial acetic acid and 8.5 g of acetylene dicarboxylic acid dimethyl ester are heated in a boiling water bath until a clear solution has formed. The solution thus obtained is then filtered over carbon. It is then left standing overnight, boiled for 10 to 15 minutes and subsequently concentrated to dryness. The residue is treated with ethyl acetate, as a result of which it crystallizes. After recrystallization from a mixture of ethyl acetate and ethanol (2:1), the 2-(pyridyl-3')-7H-1,3,4-thiadiazolo-[3,2-a]-pyrimidin-7-one-5-carboxylic acid ethyl ester thus obtained melts at 185°–187° C. with decomposition.

|  | C | H | N | S |
|---|---|---|---|---|
| calculated: | 51.65% | 3.31% | 18.53% | 10.60% |
| observed: | 51.79% | 3.64% | 18.38% | 10.83% |

EXAMPLE 18

2 g of 2-amino-5-benzyl-1,3,4-thiadiazole are introduced into 50 ml of ethanol, followed by the addition of 1.6 g of acetylene dicarboxylic acid diethyl ester. After standing overnight, the product is concentrated to dryness, 50 ml of chlorobenzene are added and the product is boiled for 1 hour. After concentration by evaporation, the residue is dissolved in ethylacetate, filtered and 2-benzyl-7H-1,3,4-thiadiazolo-[3,2-a]-pyrimidin-7-one-5-carboxylic acid ethyl ester is precipitated by the addition of ether and petroleum ether. Melting point: 116°–118° C.

|  | C | H | N | S |
|---|---|---|---|---|
| calculcated: | 57.11% | 4.16% | 13.32% | 10.15% |
| observed: | 56.99% | 4.13% | 13.08% | 9.98% |

EXAMPLE 19

8.1 g of 2-amino-5-(β-phenylethyl)-1,3,4-thiadiazole are heated with 6.8 g of acetylene dicarboxylic acid diethyl ester in 100 ml of ethanol until a clear solution has formed. After standing overnight, the solution is concentrated by evaporation to dryness. The residue crystallises on triturating with ether. 2-(β-Phenylethyl)-7H-1,3,4-thiadiazolo-[3,2-a]-pyrimidin-7-one-5-carboxylic acid ethyl ester melting at 95° to 98° C. is thus obtained.

|  | C | H | N | S |
|---|---|---|---|---|
| calculated: | 58.33% | 4.59% | 12.75% | 9.73% |

|  | C | H | N | S |
|---|---|---|---|---|
| observed: | 57.76% | 4.58% | 12.61% | 9.675 |

EXAMPLE 20

5 g of 2-aminothiazole are dissolved in 50 ml of ethanol and 8.5 g of acetylene dicarboxylic acid diethyl ester are added to the resulting solution. The mixture increases in temperature and a solid substance begins to precipitate. After standing overnight, it is filtered off, washed with a little ethanol and dried. 7H-thiazolo-[3,2-a]-pyrimidin-7-one-5-carboxylic acid ethyl ester melting at 173° to 175° C. is thus obtained in a yield of 8.2 g (85.4% of the theoretical).

7.3 g of this product are introduced into 100 ml of 1-normal hydrochloric acid and boiled under reflux for 5 hours, resulting in the formation of a clear solution which is filtered while still hot over carbon. 7H-thiazolo-[3,2-a]-pyrimidin-7-one-5-carboxylic acid crystallises out on cooling in the form of its hydrate. Yield: 4.6 g=65.3% of the theoretical; melting point: 266°-271° C. with decomposition.

EXAMPLE 21

14 g of 3-phenyl-7H-thiazolo-[3,2-a]-pyrimidin-7-one-5-carboxylic acid ethyl ester are introduced into a solution of 2.6 g of potassium hydroxide in 150 ml of ethanol. The mixture is heated until a clear solution has formed. After standing overnight, the solution is diluted with an equal volume of water, followed by filtration. The filtrate is acidified with hydrochloric acid to approximately pH 2. 3-phenyl-7H-thiazolo-[3,2-a]-pyrimidin-7-one-5-carboxylic acid crystallizes out slowly from this solution. Melting point: 161°-163° C. with decomposition.

EXAMPLE 22

10 g of 2-aminothiazole are dissolved in 150 ml of absolute ethanol and 19.8 g of acetylene dicarboxylic acid di-n-propyl ester are added to the resulting solution. The mixture is heated to 50° to 60° C. for 10 minutes. After standing overnight at room temperature the precipitate is filtered off, washed with ether and dried in vacuo. 7H-thiazolo-[3,2-a]-pyrimidin-7-one-5-carboxylic acid n-propyl ester melting at 154°-156° C. with decomposition is thus obtained in a yield of 14.5 g (61% of the theoretical).

| | $C_{10}H_{10}N_2O_3S$ (238.3) | | | |
|---|---|---|---|---|
| | C | H | N | S |
| calculated: | 50.39% | 4.23% | 11.75% | 13.46% |
| observed: | 50.15% | 4.16% | 11.65% | 13.88% |

EXAMPLE 23

The procedure is as in Example 22, except that 5 g of 2-aminothiazole are reacted with 11.3 g of acetylene dicarboxylic acid di-n-butyl ester in presence of 50 ml of absolute ethanol. 7H-thiazolo-[3,2-a]-pyrimidin-7-one-5-carboxylic acid n-butyl ester melting at 142°-144° C. is thus obtained in a yield of 8.1 g (64.3% of the theoretical).

| | $C_{11}H_{12}N_2O_3S$ (252.3) | | | |
|---|---|---|---|---|
| | C | H | N | S |
| calculated: | 52.36% | 4.79% | 11.11% | 12.71% |
| observed: | 51.78% | 4.64% | 11.18% | 13.01% |

EXAMPLE 24

A mixture of 8.8 g of 2-amino-4-phenylthiazole, 100 ml of absolute ethanol and 9.9 g of acetylene dicarboxylic acid di-n-propyl ester is heated in a water bath until a clear solution has formed. After standing for 2 days at room temperature the solution is evaporated to dryness. The residue is treated with ethyl acetate and filtered. The product is washed with ether and dried. The 3-phenyl-7H-thiazolo-[3,2-a]-pyrimidin-7-one-5-carboxylic acid n-propyl ester thus obtained melts at 201°-203° C. with decomposition. Yield: 4.5 g (28.7% of the theoretical).

| | $C_{16}H_{14}N_2O_3S$ (314.4) | | | |
|---|---|---|---|---|
| | C | H | N | S |
| calculated: | 61.12% | 4.49% | 8.01% | 10.20% |
| observed: | 61.00% | 4.54% | 8.70% | 10.24% |

EXAMPLE 25

A mixture of 8.8 g of 2-amino-4-phenylthiazole, 50 ml of absolute ethanol and 11.3 g of acetylene dicarboxylic acid di-n-butyl ester is heated to 50° to 60° C. for about 10 minutes. After standing for 2 days at room temperature the solution is evaporated to dryness. The residue is dissolved in ethyl acetate, filtered and the filtrate is mixed with an equal volume of ether. The precipitate is filtered off. 3-phenyl-7H-thiazolo-[3,2-a]-pyrimidin-7-one-5-carboxylic acid n-butyl ester is thus obtained. Yield: 5 g=30.5% of the theoretical. Melting point 152°-154° C.

| | $C_{17}H_{16}N_2O_3S$ (328.4) | | | |
|---|---|---|---|---|
| | C | H | N | S |
| calculated: | 62.17% | 4.91% | 8.54% | 9.77% |
| observed: | 61.99% | 4.79% | 8.46% | 9.94% |

EXAMPLE 26

A mixture of 5.5 g of 2-amino-5-(p-chlorophenyl)-1,3,4-thiadiazole, 100 ml of absolute ethanol and 4.5 g of acetylene dicarboxylic acid diethyl ester is heated to about 50° C. until a clear solution has formed and then left standing for 2 days. The product is filtered off, washed with ethanol and dried. Thus 2-(p-chlorophenyl)-7H-1,3,4-thiadiazolo-[3,2-a]-pyrimidin-7-one-5-carboxylic acid ethyl ester melting at 220°-222° C. with decomposition is obtained in a yield of 3.5 g (40.2% of the theoretical).

| | $C_{14}H_{10}ClN_3O_3S$ (335.8) | | | |
|---|---|---|---|---|
| | C | H | N | S |
| calculated: | 50.07% | 3.01% | 12.54% | 9.56% |
| observed: | 50.02% | 3.05% | 12.58% | 10.15% |

EXAMPLE 27

A mixture of 3.4 g 2-amino-5-methylthiazole, 70 ml of ethanol and 5.1 g of acetylene dicarboxylic acid diethyl ester is left standing for 3 days. The solution is evaporated to dryness and the residue is triturated with ethyl acetate, crystallization occurring. The product is filtered off under suction, washed with ether and dried. The 2-methyl-7H-thiazolo-[3,2-a]-pyrimidin-7-one-5-carboxylic acid ethyl ester thus obtained in a yield of 4.5 g (63% of the theoretical) melts at 119°–121° C.

| | $C_{10}H_{10}N_2O_3S$ (238.3) | | | |
|---|---|---|---|---|
| | C | H | N | S |
| calculated: | 50.39% | 4.23% | 11.75% | 13.46% |
| observed: | 50.17% | 4.20% | 11.55% | 13.96% |

EXAMPLE 28

A mixture of 6 g of 2-amino-5-cyclohexyl-1,3,4-thiadiazole, 100 ml of ethanol and 5.6 g of acetylene dicarboxylic acid diethyl ester is heated to 50° to 60° until a clear solution has formed. After standing for 2 days at room temperature, the reaction mixture is filtered and the filtrate is evaporated to dryness. 50 ml of chlorobenzene are added to the residue, followed by heating under reflux for 1 hour. After evaporation to dryness in vacuo the residue is dissolved in 50 ml of ethanol to which solution a solution of 1.85 g of potassium hydroxide in 25 ml of ethanol is added. After standing overnight 150 ml of water are added and hydrochloric acid is added to approximately pH 2. The 2-cyclohexyl-7H-1,3,4-thiadiazolo-[3,2-a]-pyrimidin-7-one-carboxylic acid crystallizes out from this solution. It may be purified by dissolving in dilute sodium hydroxide solution, treating with activated charcoal and reprecipitating by acidifying of the filtrate.

Melting point: 136° C. with decomposition.
Yield: 4.4 g=48.2% of the theoretical.

| | $C_{12}H_{13}N_3O_3S$ (279.3) | | | |
|---|---|---|---|---|
| | C | H | N | S |
| calculcated: | 51.59% | 4.70% | 15.05% | 11.47% |
| observed: | 51.10% | 4.86% | 15.24% | 11.27% |

The following compounds of general formula Ia are obtained, inter alia, by the process described above, as shown in the Examples:

2-phenyl-3-methyl-7H-thiazolo-[3,2-a]-pyrimidin-7-one-5-carboxylic acid ethyl ester
3-(p-fluorophenyl)-7H-thiazolo-[3,2-a]-pyrimidin-7-one-5-carboxylic acid ethyl ester
7H-thiazolo-[3,2-a] and 7H-1,3,4-thiadiazolo-[3,2-a]-pyrimidin-7-one-5-carboxylic acid propyl ester
3-(4'-isobutyloxyphenyl)-7H-thiazolo-[3,2-a]-pyrimidin-7-one-5-carboxylic acid methyl ester
2-(p-fluorophenyl)-7H-1,3,4-thiadiazolo-[3,2-a]-pyrimidin-7-one-5-carboxylic acid ethyl ester
2-p-tolyl-7H-1,3,4-thiadiazolo-[3,2-a]-pyrimidin-7-one-5-carboxylic acid ethyl ester
2-(4'-ethylphenyl)-7H-1,3,4-thiadiazolo-[3,2-a]-pyrimidin-7-one-5-carboxylic acid ethyl ester
2-(4'-butoxyphenyl)-7H-1,3,4-thiadiazolo-[3,2-a]-pyrimidin-7-one-5-carboxylic acid ethyl ester
2-(2',4'-dichlorophenyl)-7H-1,3,4-thiadiazolo-[3,2-a]-pyrimidin-7-one-5-carboxylic acid methyl ester
2-cyclopentyl- and 2-cyclohexyl-7H-1,3,4-thiadiazolo-[3,2-a]-pyrimidin-7-one-5-carboxylic acid ethyl ester
2-(p-chlorobenzyl)-7H-1,3,4-thiadiazolo-[3,2-a]-pyrimidin-7-one-5-carboxylic acid ethyl ester
2-ethyl-7H-1,3,4-thiadiazolo-[3,2-a]-pyrimidin-7-one-5-carboxylic acid ethyl ester
2-(n-butyl)-7H-1,3,4-thiadiazolo-[3,2-a]-pyrimidin-7-one-5-carboxylic acid methyl ester
2-(tert.-butyl)-7H-1,3,4-thiadiazolo-[3,2-a]-pyrimidin-7-one-5-carboxylic acid methyl ester
2-isopropyl-7H-1,3,4-thiadiazolo-[3,2-a]-pyrimidin-7-one-5-carboxylic acid ethyl ester From these esters, the corresponding acids and pharmaceutically acceptable salts of the type described above are obtainable.

For testing the compounds as described above, standard tests were used including: Quie et al. J. Clin. Invest., 46 (668–679 1967), and publications cited therein, also Cohn and Morse, J. exp. Med., (1959), 110. 419 (modified to use human and not mice macrophages) and Schroit et al., J. Immunol. Meth. 12 (1976), 1963–1970 modified as described under test "c"), above.

I claim:

1. A pharmaceutical drug composition useful as an immunostimulant for a mammal comprising a pharmaceutically acceptable carrier and, in an amount effective to cause an immune response in the mammal, the compound of the formula

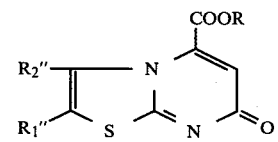

in which
R is hydrogen or $C_1$ to $C_5$ alkyl;
$R_4''$ and $R_2''$ which are the same or different, are selected from the group consisting of hydrogen, $C_1$ to $C_5$ alkyl, benzyl, phenyl ethyl, phenyl, thienyl, pyridyl, $C_5$ to $C_7$ cycloalkyl and benzyl, phenyl ethyl, phenyl, thienyl or pyridyl substituted by a halogen, alkyl or alkoxy with $C_1$–$C_4$ in the alkyl, with the proviso that $R_1''$ and $R_2''$ cannot represent at the same time hydrogen, $C_1$ to $C_5$ alkyl, unsubstituted phenyl or a heterocyclic group; or a pharmaceutically acceptable salt of such a compound.

2. The pharmaceutical drug composition of claim 1 wherein the amount of the compound in the composition useful as an immunostimulant is from about 5 to about 1000 mg.

3. A pharmaceutical drug composition of claim 2 wherein the amount of the compound in the composition useful as an immunostimulant is from about 10 to about 250 mg.

4. A pharmaceutical drug composition for treating virus infections or useful as an immunostimulant which comprises anti-virully effective or immunostimulant amount of the compound 3-phenyl-7H-thiazolo-[3,2-a]-pyrimidin-7-one-5-carboxylic acid or an ester of the acid with an alkanol of 1 to 5 carbons atoms or a pharmaceutically acceptable salt of this compound, with a pharmaceutically effective carrier.

5. A pharmaceutical drug composition for treating virus infections or useful as an immunostimulant which comprises an anti-virully effective or immunostimulant amount of the ester of the acid of claim 4 with an alkanol of 1 to 5 carbon atoms, with a pharmaceutically effective carrier.

6. A anti-viral pharmaceutical composition which comprises an effective amount for treating virus infections of mammals of a compound of the formula

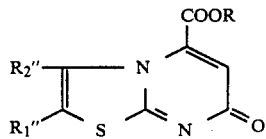

in which
R is hydrogen or $C_1$ to $C_5$ alkyl;
$R''_1$ and $R''_2$ which are the same or different are selected from the group consisting of hydrogen, $C_1$ to $C_5$ alkyl, benzyl, phenyl ethyl, phenyl, thienyl, pyridyl, $C_5$ and $C_7$ cycloalkyl and benzyl, phenyl ethyl, phenyl, thienyl or pyridyl substituted by a halogen, alkyl or alkoxy with $C_1$-$C_4$ in the alkyl, with the proviso that $R''_1$ and $R''_2$ cannot represent at the same time hydrogen, $C_1$ to $C_5$ alkyl, unsubstituted phenyl, or a heterocyclic group; or a pharmaceutically acceptable salt of such a compound, in combination with a pharmaceutically acceptable carrier.

7. The method of inducing an immune response in a warm-blooded mammal which comprises administering to the mammal an effective amount to induce an immune response of a composition of claim 1.

8. The method of claim 7 wherein the compound is administered in a dosage of about 5 to 1000 mg.

9. The method of claim 8 wherein the compound is administered in a dosage of about 10 to 250 mg.

10. A pharmaceutical drug composition for treating virus infections or useful as an immunostimulant which comprises an anti-virally effective or immunostimulant amount of a compound of the formula:

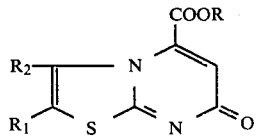

in which
R is selected from the group consisting of hydrogen or $C_1$ to $C_5$ alkyl;
$R_1$ is selected from the group consisting of benzyl, phenyl, ethyl, thienyl, pyridyl, $C_5$ and $C_7$ cycloalkyl and benzyl, phenyl ethyl, phenyl, thienyl or pyridyl substituted by a halogen, alkyl or alkoxy with $C_1$ to $C_4$ in the alkyl; and
$R_2$ is selected from the group consisting of hydrogen, $C_1$ to $C_5$ alkyl, benzyl, phenyl ethyl, phenyl, thienyl, pyridyl, $C_5$ to $C_7$ cycloalkyl and benzyl, phenyl ethyl, phenyl, thienyl or pyridyl substituted by a halogen, alkyl or alkoxy with $C_1$ to $C_4$ in the alkyl; the halogen in $R_1$ and $R_2$ being selected from chloro, bromo and fluoro;
with the proviso that $R_1$ and $R_2$ cannot at the same time represent a heterocyclic group; and the pharmaceutically acceptable salts thereof;
and a pharmaceutically effective carrier.

11. A method for treating a virus infection of a mammal comprising administering an effective amount of the drug composition of claim 10 to said mammal.

12. A method of inducing an immune response in a mammal comprising administering an effective amount of the drug composition of claim 10 to said mammal.

13. A pharmaceutical drug composition for treating virus infections or useful as an immunostimulant high comprises an anti-virally effective or immunostimulant amount of a compound of the formula:

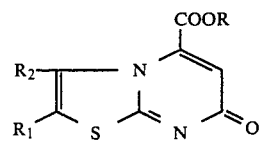

in which
R is selected from the group consisting of hydrogen, or $C_1$ to $C_5$ alkyl;
$R_1$ is selected from the group consisting of hydrogen, $C_1$ to $C_5$ alkyl, benzyl, phenyl ethyl, phenyl, thienyl, pyridyl, $C_5$ to $C_7$ cycloalkyl and benzyl, phenyl, ethyl, phenyl, thienyl or pyridyl substituted by a halogen, alkyl or alkoxy with $C_1$ to $C_4$ in the alkyl; and
$R_2$ is selected from the group consisting of benzyl, phenyl ethyl, thienyl, pyridyl, $C_5$ to $C_7$ cylcoalkyl and benzyl, phenyl ethyl, phenyl thienyl or pyridyl substituted by a halogen, alkyl or alkoxy with $C_1$ to $C_4$ in the alkyl; the halogen in $R_1$ and $R_2$ being selected from chloro, bromo and fluoro;
with the proviso that $R_1$ and $R_2$ cannot at the same time represent a heterocyclic group,
and the pharmaceutically acceptable salts thereof and a pharmaceutically effective carrier.

14. A method for treating a virus infection of a mammal comprising administering an effective amount of the drug composition of claim 13 to said mammal.

15. A method of inducing an immune response in a mammal comprising administering an effective amount of the drug composition of claim 13 to said mammal.

16. A pharmaceutical drug composition for treating virus infections or useful as an immunostimulant which comprises an anti-virally effective or immunostimulant amount of a compound of the formula:

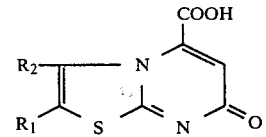

in which
$R_1$ is selected from the group consisting of hydrogen, $C_1$ to $C_5$ alkyl, benzyl, phenyl ethyl, phenyl, thienyl, pyridyl, $C_5$ to $C_7$ cycloalkyl and benzyl, phenyl ethyl, phenyl, thienyl or pyridyl substituted by a halogen, alkyl or alkoxy with $C_1$ to $C_4$ in the alkyl; and
$R_2$ is selected from the group consisting of hydrogen, $C_1$ to $C_5$ alkyl, benzyl, phenyl ethyl, phenyl, thienyl, pyridyl, $C_5$ to $C_7$ cycloalkyl and benzyl, phenyl ethyl, phenyl, thienyl or pyridyl substituted by a halogen, alkyl or alkoxy with $C_1$ to $C_4$ in the alkyl; the halogen in $R_1$ and $R_2$ being selected from chloro, bromo and fluoro;

with the proviso that $R_1$ and $R_2$ cannot represent at the same time hydrogen, $C_1$ to $C_5$ alkyl, unsubstituted phenyl, or a heterocyclic group, and the pharmaceutically acceptable salts thereof; and a pharmaceutically effective carrier.

17. A method for treating a virus infection of a mammal comprising administering an effective amount of the drug composition of claim 16 to said mammal.

18. A method of inducing an immune response in a mammal comprising administering an effective amount of the drug composition of claim 16 to said mammal.

19. A pharmaceutical drug composition for treating virus infections or useful as an immunostimulant which comprises an anti-virally effective or immunostimulant amount of a compound of the formula:

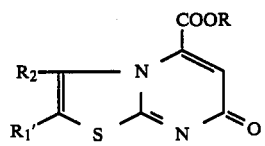

in which
R is selected from the group consisting of hydrogen, or $C_1$ to $C_5$ alkyl;
$R_1$ is selected from the group consisting of benzyl, phenyl ethyl, thienyl, pyridyl, $C_5$ to $C_7$ cycloalkyl and benzyl, phenyl ethyl, phenyl, thienyl or pyridyl substituted by a halogen, alkyl or alkoxy with $C_1$ to $C_4$ in the alkyl; and
$R_2$ is selected from the group consisting of benzyl, phenyl ethyl, thienyl, pyridyl, $C_5$ to $C_7$ cycloalkyl and benzyl, phenyl ethyl, phenyl, thienyl or pyridyl substituted by a halogen, alkyl or alkoxy with $C_1$ to $C_4$ in the alkyl; the halogen in $R_1$ and $R_2$ being selected from chloro, bromo and fluoro;
with the proviso that $R_1$ and $R_2$ cannot at the same time represent a heterocyclic group; and the pharmaceutically acceptable salts thereof; and a pharmaceutically effective carrier.

20. A method for treating a virus infection of a mammal comprising administering an effective amount of the drug composition of claim 11 to said mammal.

21. A method of inducing an immune response in a mammal comprising administering an effective amount of the drug composition of claim 19 to said mammal.

22. A pharmaceutical drug composition for treating virus infections or useful as an immunostimulant which comprises an anti-virally effective or immunostimulant amount of a compound of the formula:

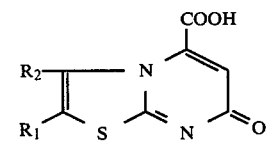

in which
$R_1$ is selected from the group consisting of benzyl, phenyl ethyl, thienyl, pyridyl, $C_5$ to $C_7$ cycloalkyl and benzyl, phenyl ethyl, phenyl, thienyl or pyridyl substituted by a halogen, alkyl or alkoxy with $C_1$ to $C_4$ in the alkyl; and
$R_2$ is selected from the group consisting of hydrogen, $C_1$ to $C_5$ alkyl, benzyl, phenyl ethyl, phenyl, thienyl, pyridyl, $C_5$ to $C_7$ cycloalkyl and benzyl, phenyl ethyl, phenyl, thienyl or pyridyl substituted by a halogen, alkyl or alkoxy with $C_1$ to $C_4$ in the alkyl; the halogen in $R_1$ and $R_2$ being selected from chloro, bromo and fluoro;
with the proviso that $R_1$ and $R_2$ cannot at the same time represent a heterocyclic group; and the pharmaceutically acceptable salts thereof; and a pharmaceutically effective carrier.

23. A method for treating a virus infection of a mammal comprising administering an effective amount of the drug composition of claim 22 to said mammal.

24. A method for treating a virus infection of a mammal comprising administering an effective amount of the drug composition of claim 22 to said mammal.

25. A pharmaceutical drug composition for treating virus infections or useful as an immunostimulant which comprises an anti-virally effective or immunostimulant amount of a compound of the formula:

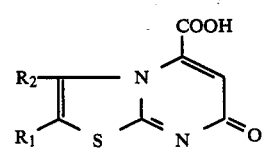

in which
$R_1$ is selected from the group consisting of hydrogen, $C_1$ to $C_5$ alkyl, benzyl, phenyl ethyl, phenyl, thienyl, pyridyl, $C_5$ to $C_7$ cycloalkyl and benzyl, phenyl ethyl, phenyl, thienyl or pyridyl substituted by a halogen, alkyl or alkoxy with $C_1$ to $C_4$ in the alkyl; and
$R_2$ is selected from the group consisting of benzyl, phenyl ethyl, thienyl, pyridyl, $C_5$ to $C_7$ cycloalkyl and benzyl, phenyl ethyl, phenyl, thienyl or pyridyl substituted by a halogen, alkyl or alkoxy with $C_1$ to $C_4$ in the alkyl; the halogen in $R_1$ and $R_2$ being selected from chloro, bromo and fluoro;
with the proviso that $R_1$ and $R_2$ cannot at the same time represent a heterocyclic group, and the pharmaceutically acceptable salts thereof;
and a pharmaceutically effective carrier.

26. A method for treating a virus infection of a mammal comprising administering an effective amount of the drug composition of claim 25 to said mammal.

27. A method of inducing an immune response in a mammal comprising administering an effective amount of the drug composition of claim 25 to said mammal.

28. A pharmaceutical drug composition for treating virus infections or useful as an immunostimulant which comprises an anti-virally effective or immunostimulant amount of a compound of the formula:

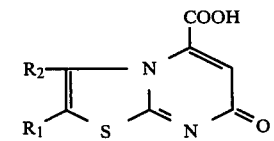

in which
$R_1$ is selected from the group consisting of benzyl, phenyl ethyl, thienyl, pyridyl, $C_5$ to $C_7$ cycloalkyl and benzyl, phenyl ethyl, phenyl, thienyl or pyridyl substituted by a halogen, alkyl or alkoxy with $C_1$ to $C_4$ in the alkyl; and R₂ is selected from the group consisting of benzyl, phenyl ethyl, thienyl, pyridyl, $C_5$ to $C_7$ cycloalkyl and benzyl, phenyl ethyl, phenyl, thienyl or pyridyl substituted by a halogen, alkyl or alkoxy with $C_1$ to $C_4$ in the alkyl; the halogen in $R_1$ and $R_2$ being selected from chloro, bromo and fluoro;

with the proviso that $R_1$ and $R_2$ cannot at the same time represent a heterocyclic group and the pharmaceutically acceptable salts thereof;

and a pharmaceutically effective carrier.

29. A method for treating a virus infection of a mammal comprising administering an effective amount of the drug composition of claim 28 to said mammal.

30. A method of inducing an immune response in a mammal comprising administering an effective amount of the drug composition of claim 28 to said mammal.

31. A pharmaceutical composition useful as an immunostimulant which comprises a pharmaceutically acceptable carrier and a thiazolo compound of the formula

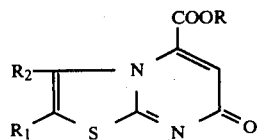

wherein R is methyl or ethyl, $R_1$ is hydrogen, methyl or phenyl and $R_2$ is bromophenyl.

32. The pharmaceutical composition useful as an immunostimulant of claim 31 wherein R is methyl and $R_1$ is methyl.

33. A method of treating a virus infection of a mammal which comprises administering an effective amount of the composition of claim 31.

34. A method of treating a virus infection of a mammal which comprises administering an effective amount of the composition of claim 32.

* * * * *